US00PP10290P

United States Patent [19]

Krans et al.

[11] Patent Number: Plant 10,290

[45] Date of Patent: Mar. 17, 1998

[54] 'MS-PRIDE' BERMUDAGRASS

[75] Inventors: Jeffrey V. Krans; H. Wayne Philley, both of Mississippi State, Miss.

[73] Assignee: Mississippi State University, Mississippi State, Miss.

[21] Appl. No.: 582,964

[22] Filed: Jan. 4, 1996

[51] Int. Cl.[6] ..... A01H 5/00

[52] U.S. Cl. ..... Plt./90

[58] Field of Search ..... Plt./90

[56] References Cited

PUBLICATIONS

Krans, J.V., et al. "Registration of 'MS–Pride' Bermudagrass" Crop Science 35:1506 (1995).

*Primary Examiner*—James R. Feyrer

*Attorney, Agent, or Firm*—Oblon, Spivak, McClelland, Maier, & Neustadt, P.C.

[57] ABSTRACT

An improved Bermudagrass plant, having superior properties, suitable for a variety of turf applications, is disclosed. The Bermudagrass is characterized by a medium to dark green color, short-head density, low seed-head density, fine-leaf texture, excellent fall color retention, excellent sod strength, average cold tolerance, good shape tolerance as compared to other Bermudagrasses, excellent dollar spot and leaf-spot resistance.

1 Drawing Sheet

BACKGROUND OF THE NEW PLANT

The present invention relates to a new and distinct variety of Bermudagrass, which has excellent turfgrass quality, good pest resistance and above-average environmental stress hardiness. The inventive Bermudagrass is suitable for use on residential lawns, sports fields, golf fairways and tees.

The inventive Bermudagrass is characterized by a medium to dark green color, high-shoot density, low seed-head density, fine-leaf texture, excellent fall color retention, excellent sod strength, average cold tolerance, good shade tolerance as compared to other bermuda grasses, excellent dollar spot and leaf-spot resistance.

BRIEF DESCRIPTION OF THE FIGURES

The plant is illustrated in FIGS. 1–6, which are color photographs of the inventive Bermudagrass.

DETAILED BOTANICAL DESCRIPTION

Figure 1:
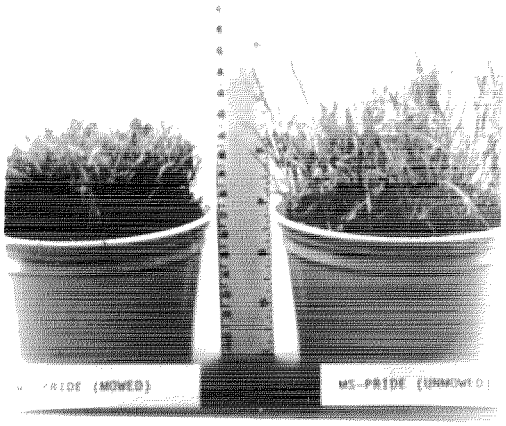
FIG. 1 reflects whole plant features of mowed and unmowed turf.

MS-Pride (experimental name MSB-10) is a distinct genotype of Cynodon that was developed and is vegatatively propagated at the Plant Science Research Center, Mississippi Agricultural and Mississippi State University, MS. MS-Pride originated from a the 5th fairway at the Vicksburg Country Club, on Aug. 20, 1980. Persons knowledgeable of Vicksburg Country Club's history said that this fairway was established with Bermudagrass seed in the mid-1960's, has existed as a golf fairway since its original planting, and had not been intentionally replanted with Bermudagrass seed, sprigs, plugs or sod since 1960. MS-Pride's origin may be from anyone of the following sources: (a) a seed within the original seed lot; (b) a seed or plant introduced unintentionally to this site; or (c) a plant that developed as a result of an environmentally selected mutation(s).

The identifying features of the original clone of MS-Pride were a medium green color, fine leaf texture, upright growth of leaves, and a high shoot density. The size of the original clone was approximately 6 ft in diameter. A 4 inch diameter plug was removed from the center of the clone and transplanted to a Bermudagrass nursery located at the Plant Science Research Center. MS-Pride was 1 of 72 ecotypes of Bermudagrass planted and maintained its original green color, fine leaf texture, upright growth of leaves, and high shoot density.

In 1986, MS-Pride was included in a regional Bermudagrass evaluation test located at 15 sites encompassing 11 states. Data was collected from 1986 to 1990. The findings from this study confirmed MS-Pirde's medium green color, high shoot density, and low seed head density. In addition, MS-Pride was found to have moderate cold tolerance, good shade tolerance, excellent dollar spot and good leafspot resistance, and at all 15 evaluation sites excellent turfgrass quality.

Morphological Description

MS-Pride has a narrow leaf width (1.1 to 1.5 mm), long leaf length (23.0 to 35.0 mm), medium internode length (8.3 to 1.07 mm) diameter (Table 1).

Seed Head Density

The seed head density of MS-Pride was measured at 3 location for 2 or 3 years depending on location (Table 2). At all three location, MS-Pride had slightly less than average seed head density compared to the other Bermudagrasses tested.

Genetic Color

The genetic color of MS-Pride was visually rated at 7 locations for 1 to 2 years depending on location (Table 3). At all locations, MS-Pride's color was rated dark to moderate green. The stolons are light green and rhizomes are white.

The color designation of MS-Pride is 7.5 GY 4/6 using a Munsell color chart rating.

Shoot Density

The shoot density of MS-Pride was measured at 2 locations for 1 or 2 years depending on location (Table 4). MS-Pride has a high shoot density which reflects a competitive growth habit, excellent wear tolerance potential, and good surface resiliency.

Shade Tolerance

The shade tolerance of MS-Pride was measured at 1 location for 2 years (Table 5). MS-Pride has better than average shade tolerance compared to the other Bermudagrasses tested.

Ploiday Level and Chromosome Number

MS-Pride's ploidy level and chromosome number were determined and compared to other Bermudagrasses (Table 6). MS-Pride was found to be a triploid with 27 chromosomes.

Turfgrass Quality Rating

The overall turf quality of MS-Pride was measured at 15 locations for 1, 2 or 3 years depending on location (Table 7). MS-Pride had higher than average turf quality compared to the other Bermudagrasses tested. The high turf quality of MS-Pride indicates that it will have widespread appeal and acceptance as a turf.

Leaf Texture

Leaf texture based on a visual rating was measured at 8 locations for 1 or 2 years depending on location (Table 8). These rating confirmed MS-Pride as a fine leaf textured Bermudagrass. The fine leaf texture of MS-Pride makes it a suitable for golf course fairways, home lawns, and sports fields.

Establishment Rate

The establishment rate of MS-Pride was measured at scheduled intervals over a 54 day period post-planting (Table 9). MS-Pride has a slow establishment rate compared to the other Bermudagrasses tested. At the end of the establishment period, MS-Pride had a 92% turf cover.

Fall Color Retention

Fall color retention of MS-Pride was measured during November at 6 locations for 1 or 3 years depending on location (Table 10). MS-Pride had excellent fall color retention compared to the other Bermudagrasses tested. This feature has special appeal in subtropical and tropical regions (deep South regions of the United States) where chilling (dormancy) of Bermudagrass is borderline. MS-Pride's better than average fall color retention makes it highly desirable in these regions.

Unmowed Height and Sod Strength

The unmowed height and sod strength of MS-Pride was measured at 1 location for 1 year and 1 location for 2 years, respectively (Table 11). MS-Pride had a low unmowed height and better than average sod strength compared to the other Bermudagrasses tested.

Low Temperature Kill

The low temperature kill of MS-Pride was measured at 1 location for 2 consecutive years (Table 12). During both years, MS-Pride had only moderate low temperature kill compared to the other Bermudagrasses tested.

Disease Resistance

MS-Pride's resistance to leafspot (Helminthosporium spp.) and dollar spot (Sclerotinia spp.) was measured at 1 location for 2 years (Table 13). MS-Pride's ratings for leafspot and dollar spot resistance were better than average compared to other Bermudagrasses tested.

Distinguishing Features of MS-Pride

Figure 2:
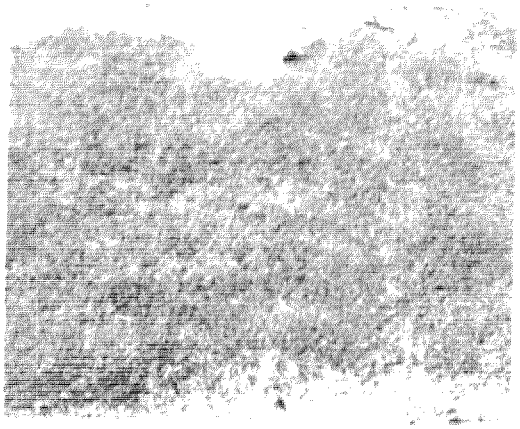
FIG. 2 is a photograph of a field plot of mowed turf.
Figure 3:
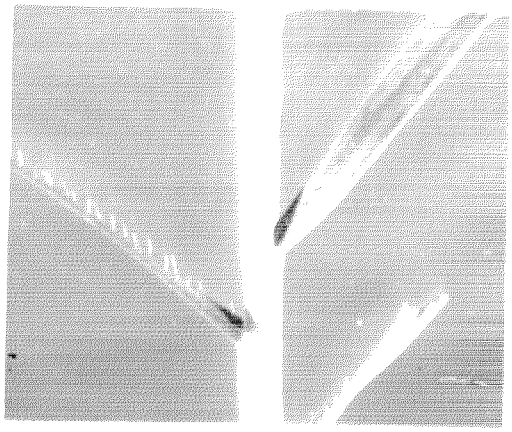
FIG. 3 is a photograph of a typical inflorescence structure showing three racemes per stalk.
Figure 4:
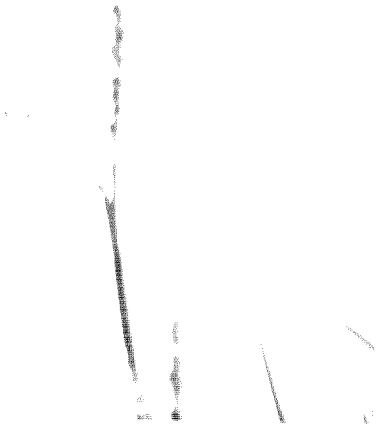
FIG. 4 is a photograph reflecting the leaf blade and sheath features of the inventive plant.
Figure 5:
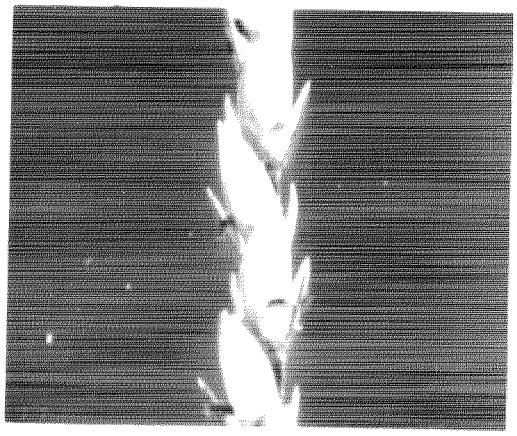
FIG. 5 is a photograph reflecting an abaxial view of spikelets of the inventive Bermudagrass.
Figure 6:
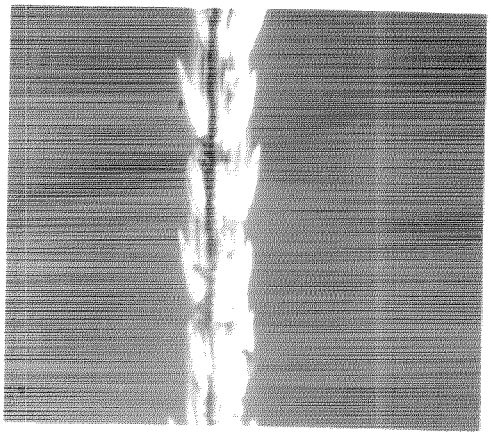
FIG. 6 is a photograph reflecting an adaxial view of spikelets of the inventive Bermudagrass.

MS-Pride can be distinguished by morphological and turf performance characteristics. MS-Pride has high turf density and quality as illustrated in pot and field plot culture (FIGS. 1 and 2). MS-Pride's shoot structure is pilose on the abaxial leaf blade surface, pubescence tufted at the ligule margins, and glabrous on the adaxial leaf surface and sheath (FIG. 4). MS-Pride has a raceme inflorescence structure with 3 racemes attached per stalk in a single whorl (FIG. 3). Average spikelet density is one spikelet attached every 0.75 mm on the raceme stalk. Length of an average spikelet is 2.5 mm with glumes extending from ½ to ⅔ the length of a floret (FIGS. 5 and 6). The flower of MS-Pride has a purple stigma and yellow anthers.

Compared to MS-Choice, Midiron, Texturf 10, Tufcote, and MS-Express, MS-Pride has a narrower leaf width (Table 1). Leaf length of MS-Pride is longer than MS-Choice, Texturf 10, and Tifgreen. There are few differences in internode length between MS-Pride and the other Bermudagrasses tested; however, diameters of MS-Pride's internodes and nodes were smaller compared to those found in MS-Choice, Midiron, Text 10, and Tifgreen. Seed head density of MS-Pride was less than Tifgreen, Texturf 10, Tufcote, Midiron, MS-Express, and Arizona Common (Table 2).

MS-Pride has turf performance characteristics that distinguish it from other Bermudagrasses. MS-Pride has sod strength significantly greater than all other Bermudagrasses tested (Table 5). This feature is important because MS-Pride plants lack viable seed and they must rely on sod for propagation. The high sod strength of MS-Pride turf provides efficient sod harvest, handling, and installation.

MS-Pride, light all turf grasses, has a tendency to thatch. The tendency to thatch in this grass is limited. The thatch is comprised of dead leaves, dead or living stolons and dead or living crowns. In contrast to other Bermudagrasses, MS-Pride has an average tendency to thatch.

The mowing height range for MS-Pride is from ½–2 inches. This Bermudagrass may not be suitable for use for golf putting greens. Another distinctive turf feature of MS-Pride is excellent shade tolerance (Table 5). MS-Pride has significantly better shade tolerance than Tifway, Tifway II, Texturf 10, Tufcote, Common, and Midiron Bermudagrasses. Shade tolerance, like sod strength, is a key feature that given MS-Pride high turf desirability.

Other performance characteristics of MS-Pride ranked above average compared to the other grasses tested. Some of these features are high turf quality, good shoot density, good fall color retention, fine leaf texture, good resistance to low temperature kill, and good disease resistance. The following characteristics are also distinctive:

(a) Leaf color is line green and rated 7.5 GY 4/6 based on a Munsell® color chart for plant tissue. There is no anthocyanin pigmentation expressed in leaves during the fall. The average leaf width is 1.3 mm and average length 29.0 mm.

(b) The grass has a dense canopy of leaves erect from a prostrate base of creeping, strong stolons. Rhizomes are stout, branched profusely. Stolon color is 5 GY 7.8 based on a Munsell® color chart for plant tissue. There is no anthocyanin pigmentation expressed in stolons during the fall. The average stolon internode diameter is 0.65 mm, the average stolon node diameter is 0.85 mm, and average stolon internode length is 11.8 mm.

(c) The grass has an extensive fibrous root system initiated from the nodes of stolons and rhizomes.

(d) Leaves are folded in the bud shoot; the blades are mostly flat or slightly V-shaped with a only the midvein visible; and the leaf tip is tapered to an acute apex.

(e) The grass has a moderate frequency of inflorescence formation having an average density of 450 inflorscence per square meter. Average height of culms is 35 mm. The inflorescence consists of 2 to 3 digitate spikes at the top of the main stem, folded down at a 30 to 40 degree angle from vertical, spikelets sessiled and closely appressed. The average length of a spike is 23 mm.

(f) The grass blade is pilose on the abaxial and glabrous on adaxial surface. The ligule consists of a fringe of hairs. The sheath is glabrous, split with margins overlapping, and pubescence tufted at the side of the ligule. The collar is a continuous narrow band, glabrous and auricles are absent.

(g) The spikelets are glabrous in two rows, blunt at their base and pointed at their tips. Spikelets are attached an average distance of 0.75 mm along the spikes. The length of an average spikelet is 2.5 mm with glumes extending ½ to ⅔ the length of a floret. The spikelet has stigmas of light purple-red color rated as a 5 RP 7/8 based on a Munsell® color chart for plant tissue.

(h) The grass has a somatic chromosome number of 27 and classed as a tripolid.

TABLE 1

A quantitative comparison of morphological features that describe the whole plant morphology of MS-Pride and eight other bermudagrasses.

| Bermudagrass Entry | Leaf Width | Leaf Length | Internode Length | Internode Diameter | Node Diameter |
|---|---|---|---|---|---|
| | mm | | | | |
| MS-Pride | 1.3 | 29.0 | 11.8 | 0.65 | 0.85 |
| MS-Choice | 2.4 | 22.6 | 10.2 | 1.43 | 1.65 |
| Midiron | 2.3 | 35.8 | 15.7 | 1.00 | 1.35 |
| Texturf 10 | 1.8 | 22.9 | 9.4 | 1.28 | 1.28 |
| Turfcote | 1.7 | 33.7 | 12.9 | 1.10 | 1.33 |
| MS-Express | 1.8 | 23.8 | 11.1 | 0.95 | 1.25 |
| Tifgreen | 1.3 | 22.3 | 9.4 | 0.90 | 1.22 |
| Tifway II | 1.3 | 27.2 | 10.9 | 0.64 | 0.85 |
| Tifway | 1.2 | 28.2 | 11.8 | 0.67 | 0.89 |
| LSD (.05) | .22 | 5.66 | 3.02 | 0.172 | 0.222 |
| Mean | 1.65 | 27.27 | 11.47 | 0.93 | 1.18 |

TABLE 2

Comparative seed head density of MS-Pride and nine other bermudagrasses.

| Bermudagrass Entry | Field Plot Locations: Starkville Mississippi | Las Cruces New Mexico | Blacksburg Virginia |
|---|---|---|---|
| MS-Choice | 8.8[1] | 9.0 | 9.0 |
| Tifgreen | 4.0 | 4.7 | 6.2 |
| Tifway | 7.0 | 7.8 | 8.2 |
| Tifway II | 7.3 | 7.8 | 7.8 |
| Texturf 10 | 5.3 | 8.0 | 6.7 |
| Tufcote | 7.5 | 5.3 | 7.7 |
| Midiron | 5.7 | 5.0 | 7.3 |
| MS-Pride | 7.3 | 7.9 | 7.7 |
| MS-Express | 4.3 | 5.1 | 6.5 |
| Arizona Common | 4.7 | 5.9 | 6.7 |
| LSD (.05) | 0.77 | 0.67 | 0.82 |
| Mean | 6.2 | 6.6 | 7.4 |
| Cultivar X Year interaction. | * | ** | ** |
| Years data was collected. | 1987 1988 | 1986 1987 1988 | 1987 1988 |

[1]Seed head density rating based on a 1 to 9 scale; with 1 = high seed head density adn 9 = no seed heads.
*,** Significant at the .05 and .01 level of probability, respectively.

TABLE 3

Comparative genetic color of MS-Pride and nine other bermudagrasses.

| Bermudagrass Entry | Field Plot Location: Tucson Arizona | Santa Ana California | Gainsville Florida | Starkville Mississippi |
|---|---|---|---|---|
| MS-Choice | 7.0[1] | 9.0 | 7.3 | 7.7 |
| Tifgreen | 6.3 | 7.0 | 5.2 | 5.0 |
| Tifway | 6.7 | 8.0 | 7.0 | 6.3 |
| Tifway II | 6.3 | 8.0 | 6.8 | 7.0 |
| Texturf 10 | 6.3 | 7.7 | 5.8 | 5.3 |
| Tufcote | 6.7 | 6.7 | 5.8 | 5.0 |
| Midiron | 6.7 | 7.7 | 5.7 | 5.3 |
| MS-Pride | 6.0 | 7.7 | 6.8 | 7.0 |
| MS-Express | 6.3 | 7.7 | 6.2 | 5.0 |
| Arizona Common | 5.3 | 5.7 | 5.2 | 5.0 |
| LSD (.05) | NS | 0.75 | 0.55 | 0.65 |
| Mean | 6.4 | 7.5 | 6.2 | 5.9 |
| Cultivar X Year interaction. | | | ** | |
| Years data was collected. | 1987 | 1987 | 1987 1988 | 1988 |

| Bermudagrass Entry | Field Plot Location: Las Cruces New Mexico | Stilwater Oklahoma | Cleveland Texas |
|---|---|---|---|
| MS-Choice | 7.5 | 8.0 | 8.7 |
| Tifgreen | 6.8 | 6.3 | 7.7 |
| Tifway | 7.0 | 7.7 | 9.0 |
| Tifway II | 7.7 | 6.0 | 8.0 |
| Texturf 10 | 7.0 | 7.3 | 8.0 |
| Tufcote | 7.2 | 4.7 | 7.3 |
| Midiron | 6.3 | 6.7 | 7.0 |
| MS-Pride | 7.7 | 6.3 | 8.7 |
| MS-Express | 6.7 | 6.3 | 7.7 |
| Arizona Common | 5.5 | 6.0 | 6.7 |
| LSD (.05) | NS | 1.08 | 0.80 |
| Mean | 6.9 | 6.6 | 7.9 |

TABLE 3-continued

Comparative genetic color of MS-Pride and nine other bermudagrasses.

| | | | |
|---|---|---|---|
| Cultivar X Year interaction. | NS | | |
| Years data was collected. | 1986<br>1987 | 1988 | 1988 |

[1]Genetic color rating based on a 1 to 9 scale; with 1 = light green color and 9 = dark green color.
*,** Significant at the .05 and .01 level of probability, respectively.

TABLE 4

Comparative shoot density of MS-Pride and nine other bermudagrasses.

| Bermudagrass Entry | Field Plot Location: Las Cruces New Mexico | Stillwater Oklahoma |
|---|---|---|
| MS-Choice | 8.4[1] | 8.0 |
| Tifgreen | 8.4 | 7.7 |
| MS-Pride | 8.1 | 7.3 |
| Texturf 10 | 7.8 | 8.0 |
| Tifway | 7.7 | 7.7 |
| Midiron | 7.9 | 7.0 |
| Tifway II | 7.3 | 7.7 |
| MS-Express | 7.3 | 7.3 |
| Tufcote | 6.3 | 7.7 |
| Arizona Common | 3.9 | 6.0 |
| LSD (0.05) | 0.61 | 0.95 |
| Mean | 7.3 | 7.5 |
| Entry x Year Interaction | ** | NA |
| Year(s) data was recorded | 1986<br>1987 | 1987 |

[1]Shoot density rating based on a visual scale; with 1 = low density and 9 = high density.
*, ** Significant at the 0.05 and 0.01 level of probability, respectively.

TABLE 5

Comparative shade tolerance of MS-Pride and nine other bermudagrasses[1].

| Bermudagrass Entry | Shade Tolerance |
|---|---|
| MS-Choice | 4.9[2] |
| MS-Pride | 4.5 |
| Tifgreen | 4.3 |
| MS-Express | 4.3 |
| Tifway II | 3.8 |
| Tifway | 3.7 |
| Texturf 10 | 3.5 |
| Tufcote | 3.4 |
| Arizona Common | 2.5 |
| Midiron | 2.1 |
| LSD (0.05) | 0.39 |
| Mean | 3.7 |
| Cultivar X Year interaction | ** |
| Years data was collected | 1987<br>1988 |

[1]Field plots located in Starkville, MS.
[2]Shade tolerance based on a visual scale of 1 to 9: with 9 = excellent shade tolerance and 1 = poor shade tolerance.
*, ** Significant at the 0.05 and 0.01 level of probability, respectively.

TABLE 6

The ploidy level and chromosome number of MS-Pride and nine other bermudagrasses.

| Bermudagrass Entry | Ploidy Level | Chromosome Number |
|---|---|---|
| MS-Choice | Tetraploid | 36[1] |
| Texturf 10 | | 36 |
| Turfcote | | 36 |
| Midiron | | 36 |
| Arizona Common | | 36 |
| MS-Express | Triploid | 27 |
| MS-Pride | | 27 |
| Tifgreen | | 27 |
| Tifway | | 27 |
| Tifway II | | 27 |

[1]Chromosome numbers were determined using squashes of root tips.

TABLE 7

Comparative turfgrass quality of MS-Pride and nine other bermudagrasses.

| Bermudagrass Entry | Field Plot Location: Tucson Arizona | Santa Ana California | Riverside California | Gainsville Florida |
|---|---|---|---|---|
| MS-Choice | 7.5[1] | 6.3 | 4.9 | 5.7 |
| Tifgreen | 7.3 | 5.8 | 5.4 | 4.8 |
| Tifway | 7.8 | 6.5 | 5.5 | 5.8 |
| Tifway II | 7.9 | 6.5 | 5.7 | 5.7 |
| Texturf 10 | 7.8 | 5.8 | 5.1 | 5.1 |
| Tufcote | 7.3 | 5.4 | 5.2 | 5.6 |
| Midiron | 6.2 | 5.8 | 4.9 | 4.9 |
| MS-Pride | 8.3 | 6.5 | 5.3 | 6.0 |
| MS-Express | 7.8 | 5.9 | 5.8 | 5.2 |
| Arizona Common | 5.5 | 4.4 | 4.7 | 4.9 |
| LSD (.05) | 0.54 | 0.33 | 0.55 | 0.32 |
| Mean | 7.3 | 5.9 | 5.2 | 5.4 |
| Cultivar X Year interaction. | | ** | NS | ** |
| Year(s) data was collected. | 1988 | 1986<br>1987 | 1986<br>1987<br>1988 | 1987<br>1988<br>1988 |

| Bermudagrass Entry | Field Plot Location: Manhattan Kansas | Wichita Kansas | Baton Rogue Louisiana | Silver Springs Maryland |
|---|---|---|---|---|
| MS-Choice | 6.9 | 8.0 | 7.0 | 6.0 |
| Tifgreen | 6.9 | 7.8 | 7.7 | 6.2 |
| Tifway | 6.3 | 8.2 | 7.6 | 6.3 |
| Tifway II | 6.5 | 8.4 | 7.6 | 6.4 |
| Texturf 10 | 6.7 | 7.9 | 6.9 | 5.3 |
| Tufcote | 6.9 | 7.7 | 7.3 | 5.8 |
| Midiron | 6.7 | 7.7 | 6.7 | 5.4 |
| MS-Pride | 6.5 | 8.3 | 7.5 | 6.4 |
| MS-Express | 6.8 | 8.1 | 7.6 | 7.7 |
| Arizona Common | 5.0 | 5.9 | 6.3 | 5.0 |
| LSD (.05) | 0.38 | 0.30 | 0.59 | NS |
| Mean | 6.5 | 7.8 | 7.2 | 6.1 |
| Cultivar X Year interaction. | ** | ** | * | |
| Year(s) data was collected. | 1987<br>1988 | 1986<br>1987 | 1987<br>1988<br>1988 | 1988 |

| Bermudagrass Entry | Field Plot Location: Starkville Mississippi | Las Cruces New Mexico | Cleveland Texas | Beltsville Maryland |
|---|---|---|---|---|
| MS-Choice | 6.1[1] | 7.3 | 8.0 | 7.0 |
| Tifgreen | 7.4 | 6.3 | 9.0 | 7.3 |
| Tifway | 6.7 | 7.0 | 7.7 | 6.6 |

TABLE 7-continued

Comparative turfgrass quality of MS-Pride and nine other bermudagrasses.

| | | | | |
|---|---|---|---|---|
| Tifway II | 6.9 | 7.5 | 8.0 | 6.8 |
| Texturf 10 | 5.6 | 6.8 | 5.7 | 6.5 |
| Tufcote | 5.5 | 6.2 | 5.7 | 6.7 |
| Midiron | 5.1 | 6.5 | 5.3 | 5.8 |
| MS-Pride | 6.9 | 7.2 | 8.0 | 6.9 |
| MS-Express | 7.6 | 6.7 | 8.7 | 7.0 |
| Arizona Common | 4.1 | 3.8 | 4.0 | 4.5 |
| LSD (.05) | 0.19 | 0.49 | 1.14 | 0.38 |
| Mean | 6.2 | 6.5 | 7.0 | 6.5 |
| Cultivar X Year interaction. | ** | ** | NA | ** |
| Year(s) data was collected. | 1986<br>1987<br>1988 | 1986<br>1987<br>1988 | 1988 | 1986<br>1987<br>1988 |

| | Field Plot Location | | |
|---|---|---|---|
| Bermudagrass Entry | Blacksburg Virginia | Blackstone Virginia | Virginia Beach Virginia |
| MS-Choice | 5.9 | 6.8 | 6.7 |
| Tifgreen | 5.9 | 6.8 | 6.2 |
| Tifway | 6.5 | 7.0 | 6.3 |
| Tifway II | 6.1 | 6.8 | 6.9 |
| Texturf 10 | 6.0 | 6.6 | 5.7 |
| Tufcote | 5.8 | 6.4 | 4.9 |
| Midiron | 5.0 | 5.8 | 5.9 |
| MS-Pride | 5.8 | 6.8 | 6.4 |
| MS-Express | 6.5 | 6.8 | 6.0 |
| Arizona Common | 4.2 | 5.0 | 3.9 |
| LSD (.05) | 0.43 | 0.38 | 0.77 |
| Mean | 5.8 | 6.5 | 5.9 |
| Cultivar X Year interaction. | * | ** | NA |
| Year(s) data was collected. | 1986<br>1987<br>1988 | 1986<br>1988 | 1986 |

[1]Turfgrass quality ratings based on a 1 to 9 scale with 1 = poor turfgrass quality and 9 = excellent turf quality.
*, ** Significant at the .05 and .01 level of probability, respectively.

TABLE 8

Comparative leaf texture of MS-Pride and nine other bermudagrasses.

| | Field Plot Locations | | | |
|---|---|---|---|---|
| Cultivar | Tucson Arizona | Wichita Kansas | Gainsville Florida | Starkville Mississippi |
| MS-Choice | 5.3[1] | 6.7 | 5.7 | 5.0 |
| Tifgreen | 7.3 | 9.0 | 7.5 | 7.7 |
| Tifway | 7.0 | 7.7 | 7.8 | 6.0 |
| Tifway II | 6.3 | 8.3 | 8.2 | 6.0 |
| Texturf 10 | 5.7 | 8.0 | 5.5 | 5.0 |
| Tufcote | 5.7 | 6.0 | 7.0 | 5.0 |
| Midiron | 5.3 | 4.0 | 5.8 | 5.0 |
| MS-Pride | 6.7 | 7.3 | 8.0 | 6.0 |
| MS-Express | 7.7 | 9.0 | 7.3 | 8.0 |
| Arizona Common | 4.3 | 3.7 | 2.7 | 4.3 |
| LSD (.05) | 0.92 | 0.68 | 1.01 | 0.43 |
| Mean | 6.1 | 7.0 | 6.6 | 5.8 |
| Cultivar X Year interaction. | | | ** | |
| Year(s) data was collected. | 1987 | 1986 | 1987<br>1988 | 1988 |

| | Field Plot Locations | | |
|---|---|---|---|
| Cultivar | Las Cruces New Mexico | Baton Rogue Louisiana | Virginia Virginia |
| MS-Choice | 6.5 | 6.3 | 4.7 |
| Tifgreen | 9.0 | 9.0 | 7.0 |

TABLE 8-continued

Comparative leaf texture of MS-Pride and nine other bermudagrasses.

| | | | |
|---|---|---|---|
| Tifway | 8.2 | 9.0 | 6.0 |
| Tifway II | 8.3 | 9.0 | 5.7 |
| Texturf 10 | 5.8 | 6.3 | 5.7 |
| Tufcote | 6.7 | 9.0 | 3.7 |
| Midiron | 6.8 | 7.7 | 4.3 |
| MS-Pride | 8.5 | 9.0 | 6.0 |
| MS-Express | 8.8 | 9.0 | 6.0 |
| Arizona Common | 4.2 | 6.3 | 2.3 |
| LSD (.05) | 0.79 | 0.79 | 1.19 |
| Mean | 7.3 | 8.1 | 5.1 |
| Cultivar X Year interaction. | ** | | |
| Year(s) data was collected. | 1986<br>1987 | 1988 | 1988 |

[1]Leaf texture rating based on a 1 to 9 scale; with 1 = coarse leaf texture and 9 = fine leaf texture.
*, ** Significant at the 0.05 and 0.01 level of probability, respectively.

TABLE 9

Comparative establishment rate of MS-Pride and other bermudagrasses.

| | Days After Planting[1] | | | | |
|---|---|---|---|---|---|
| Bermudagrass Entry | 26 | 33 | 40 | 47 | 54 |
| | % cover | | | | |
| Arizona Common | 65.0[2] | 66.7 | 90.0 | 97.7 | 100.0 |
| Midiron | 36.7 | 43.3 | 76.7 | 91.7 | 100.0 |
| MS-Choice | 36.7 | 38.3 | 71.7 | 88.3 | 100.0 |
| Tifgreen | 35.0 | 41.7 | 80.0 | 91.7 | 100.0 |
| MS-Express | 35.3 | 45.0 | 86.7 | 88.3 | 98.3 |
| Tufcote | 35.0 | 40.0 | 76.7 | 91.0 | 98.3 |
| Texturf 10 | 31.7 | 43.3 | 73.3 | 88.3 | 98.3 |
| Tifway | 25.0 | 30.0 | 51.7 | 66.7 | 93.3 |
| Tifway II | 21.7 | 28.3 | 41.7 | 73.3 | 93.3 |
| MS-Pride | 20.0 | 28.3 | 51.7 | 66.7 | 91.7 |
| LSD (0.05) | 14.3 | 14.7 | 18.7 | 20.3 | 8.2 |
| Mean | 34.2 | 40.5 | 70.0 | 84.4 | 97.3 |

[1]All entries were planted on 6-20-86 using 2 inch diameter plugs spaces on 1 ft intervals. Plots were located in Starkville, MS and plot size was 5 × 10 ft.
[2]The % cover was based on a visual estimation of the % of the plot area covered by vegetation.

TABLE 10

Comparative fall color retention of MS-Pride and nine other bermudagrasses.

| | Field Plot Location | | | | |
|---|---|---|---|---|---|
| Bermuda-grass Entry | Beltsville Maryland | Raleigh North Carolina | Starkville Mississ-ippi | Las Cruces New Mexico | Loc. 2 New Mexico |
| MS-Pride | 5.3[1] | 6.7 | 6.5 | 4.3 | 5.3 |
| Tifway | 4.8 | 6.7 | 6.2 | 4.6 | 5.7 |
| Tifway II | 4.5 | 7.3 | 6.5 | 4.4 | 5.7 |
| Tufcote | 2.8 | 6.3 | 5.3 | 3.2 | 3.3 |
| Midirion | 2.3 | 3.7 | 4.2 | 3.1 | 3.3 |
| Texturf 10 | 2.2 | 5.3 | 3.2 | 2.6 | 5.0 |
| MS-Choice | 2.0 | 5.7 | 4.2 | 3.4 | 4.3 |
| Tifgreen | 2.0 | 6.3 | 3.2 | 2.0 | 4.0 |
| MS-Express | 1.7 | 6.7 | 3.0 | 2.1 | 4.3 |
| Arizona Common | 1.7 | 5.7 | 4.5 | 3.4 | 2.3 |
| LSD (0.05) | 0.68 | 1.54 | 0.43 | 0.76 | 1.74 |
| Mean | 2.9 | 6.0 | 4.7 | 3.3 | 4.3 |

TABLE 10-continued

Comparative fall color retention of MS-Pride and nine other bermudagrasses.

| Bermuda-grass Entry | Field Plot Location: Beltsville Maryland | Raleigh North Carolina | Starkville Mississippi | Las Cruces New Mexico | Loc. 2 New Mexico |
|---|---|---|---|---|---|
| Cultivar x Year interaction | ** | NA | ** | ** | NA |
| Year(s) data was collected | 1986 1987 | 1986 | 1986 1988 | 1986 1987 1988 | 1988 |

[1]Color ratings based on a visual scale of color with; 9 = green color and 1 = brown color.

*, ** Significant at the 0.05 and 0.01 level of probability, respectively.

TABLE 11

Comparative height of unmowed plots and sod strength of MS-Pride and nine other bermudagrasses.

| Bermudagrass Entry | Plant Measurement: Unmoved Height cm | Sod Strength lbs |
|---|---|---|
| Arizona Common | 31.7[1] | 26.8[2] |
| Tufcote | 8.7 | 39.3 |
| Midiron | 5.7 | 39.5 |
| Tifway II | 5.0 | 121.5 |
| MS-Choice | 4.3 | 65.5 |
| Texturf 10 | 4.3 | 77.8 |
| Tifway | 4.3 | 95.2 |
| MS-Express | 4.0 | 86.7 |
| MS-Pride | 4.0 | 157.7 |
| Tifgreen | 3.3 | 74.7 |
| LSD (0.05) | 1.8 | 34.5 |
| Mean | 7.5 | 78.5 |
| Entry x Year Interaction | NA | NS |
| Year(s) data was collected | 1986 | 1987 1988 |
| Location | Las Cruces New Mexico | Starkville Mississippi |

[1]The shoot height was determined by measuring the height of the grass at its maximum length above the soil surface.

[2]Sod strength was determined by measuring the amount of force (lbs) required to shear an 18 × 24 × 1" section of sod.

TABLE 12

Comparative turf mortality due to winter kill of MS-Pride and nine other bermudagrasses[1].

| Bermudagrass Entry | Year: 1987 % turf mortality | 1988 % turf mortality |
|---|---|---|
| Tufcote | 0[2] | 0 |
| Tifgreen | 3.3 | 1.7 |
| MS-Express | 1.7 | 5.0 |
| Texturf 10 | 3.3 | 10.0 |
| MS-Pride | 5.0 | 25.0 |
| Midiron | 11.7 | 11.7 |
| Tifway | 5.0 | 36.7 |
| Tifway II | 5.0 | 36.7 |
| MS-Choice | 11.7 | 36.7 |
| Arizona Common | 35.0 | 88.3 |
| LSD (0.05) | 11.6 | 12.9 |
| Mean | 8.2 | 25.2 |

[1]Field plot were located in Beltsville, MD.

[2]The % of plot area lost to low temperature killed was based on a visual evaluation of turf lost immediately following spring green-up in May.

TABLE 13

Comparative leafspot (Helminthosporium spp.) and dollarspot (Sclerotinia spp.) disease resistance of MS-Pride and nine other bermudagrasses.

| Bermudagrass Entry | Disease Rating: Leaf Spot | Dollar Spot |
|---|---|---|
| MS-Pride | 8.8[1] | 8.4 |
| MS-Express | 8.7 | 7.7 |
| Tifgreen | 8.3 | 7.3 |
| Tifway II | 8.3 | 8.5 |
| Texturf 10 | 8.2 | 8.7 |
| Tifway | 8.2 | 8.7 |
| MS-Choice | 7.9 | 6.4 |
| Midiron | 7.8 | 8.7 |
| Tufcote | 7.0 | 8.8 |
| Arizona Common | 6.2 | 8.6 |
| LSD (0.05) | 0.73 | 0.83 |
| Mean | 7.9 | 8.2 |
| Entry x Year Interaction | ** | ** |
| Year(s) data was collected | 1986 1988 | 1986 1988 |

[1]Disease rating based on a visual scale of 1 to 9; with 9 = no disease damage (excellent disease resistance) and 1 = high incidence of disease damage (poor disease resistance).

*, ** Significant at the 0.05 and 0.01 level of probability, respectively.

What is claimed is:

1. A Bermudagrass plant substantially as described and illustrated in the specification herein.

* * * * *